United States Patent [19]

Sakamaki et al.

[11] Patent Number: 4,675,162

[45] Date of Patent: Jun. 23, 1987

[54] AUTOMATIC CHEMICAL ANALYZING APPARATUS

[75] Inventors: Takeshi Sakamaki, Yaita; Fumio Watanabe, Hachioji, both of Japan

[73] Assignee: Kabushiki Kaisha Toshiba, Kawasaki, Japan

[21] Appl. No.: 725,792

[22] Filed: Apr. 22, 1985

[30] Foreign Application Priority Data

Apr. 21, 1984 [JP] Japan ................................. 59-80795

[51] Int. Cl.⁴ .......................................... G01N 35/04
[52] U.S. Cl. ...................................... 422/65; 422/67; 436/47; 436/48
[58] Field of Search .............. 422/63, 65, 67; 436/47, 436/48

[56] References Cited

U.S. PATENT DOCUMENTS

| | | | |
|---|---|---|---|
| 4,058,367 | 11/1977 | Gilford | 422/67 |
| 4,265,855 | 5/1981 | Mandle | 422/65 |
| 4,383,041 | 5/1983 | Kutsusawa et al. | 422/65 |

FOREIGN PATENT DOCUMENTS 2095829 10/1982 United Kingdom ................. 422/63

Primary Examiner—Michael S. Marcus
Attorney, Agent, or Firm—Oblon, Fisher, Spivak, McClelland & Maier

[57] ABSTRACT

An automatic chemical analyzing apparatus including a cuvette assembly having a plurality of rows of reaction tubes arranged in respective sample magazines, each sample magazine being conveyed sequentially in a direction perpendicular to the transverse row of reaction tubes, and then in a direction parallel thereto so as to complete a reaction channel, during which the samples to be analyzed in the magazine are treated and analyzed a predetermined number of times by passing through a photometer. Adjacent the reaction channel is provided a preparation channel for cleaning and drying of reaction tubes and/or for adding of samples and reagents to the cleaned and dried tubes. Sample magazines are selectively transferrable from the reaction chamber to the preparation chamber upon completion of testing of the samples.

8 Claims, 8 Drawing Figures

AUTOMATIC CHEMICAL ANALYZING APPARATUS

BACKGROUND OF THE INVENTION

1. Field of the Invention

This invention generally relates to an automatic chemical analyzing apparatus and in particular to an improved multi-item automatic chemical analyzing apparatus having enhanced analyzing capability.

2. Discussion of Background

For chemical analyses carried out in series, there are used to an increasing extent chemical analyzers which carry out automatically the sampling, the adding of reagents, the provision for the suitable reaction conditions occurring in the course of analyses, the measurement, the display and recordation of the data. Such devices are used, e.g. in hospitals and clinics, where a large number of measurements must be carried out in a short time.

Many automatic chemical analyzing apparatus, such as disclosed in U.S. Pat. No. 3,622,279, in current use can simultaneously analyze one or more test items. Such analyzers include a plurality of reaction lines used for respective specific tests without any item change, and are called a multi-channel automatic chemical analyzer.

An analyzer as shown in U.S. Pat. No. 3,660,638 includes only one reaction line (meaning a path along which reaction tubes are arranged in a line or a pipe through which samples spaced by bubbles pass) to take a multi-item (multi-component) measurement. Such a known one-line automatic chemical analyzer is of a type in which each of the samples is successively analyzed in terms of a plurality of specific items, or a type in which the same reaction line is used and all associated samples are first analyzed in terms of one item and then in terms of another item after the end of analysis of the one item.

In the above-mentioned apparata, the multi-channel automatic chemical analyzer is operated at very poor efficiency with disadvantageous operation of unnecessary reaction lines for the non-selected test items of each sample because the typical samples, being individually observed, do not require test of all of the possible items capable of being tested. Further, in the single channel automatic chemical analyzer, it takes more time to obtain results about all the test items of one sample if the test items increase in number with respect to the individual samples, or the samples to be analyzed increase, and it is difficult to eliminate the contamination between the different reagents supplied in series to the same cuvette because of a failure to clean completely the cuvette in the elapsed time.

In addition, many chemical reactions must be analyzed over a period of 5 minutes or more so as to measure the rate of reaction with high accuracy, so that the analysis generally proceeds slowly. This is contrary to increasing the sample processing speed. However, this requirement is very important to achieve an accurate measurement of the samples.

SUMMARY OF INVENTION

Accordingly, an object of the present invention is to provide an improved automatic chemical analyzing apparatus in which many samples having different test items are analyzed in such a manner that any reaction line cuvette can be selected for any analytical test being conducted on a sample and so that there are no unused cuvettes in any magazine in the apparatus in the reaction channel.

Another object of the invention is to increase the flexibility of the automatic chemical analyzing apparatus so that each tube in a magazine may include a selected sample and reagent fluid, which may vary from tube to tube, for any analysis without regard to the number of tests or reagents.

It is still another object of the present invention to provide an automatic chemical analyzing apparatus having a large number of tubes, called cuvettes, arranged in a small space, thereby to provide an analyzing apparatus having reduced size and capable of analyzing a large number of samples in a short time.

These and other objects are achieved according to the present invention by providing a novel automatic chemical analyzing apparatus wherein the samples or specimens each added with reagent in the cuvettes are individually irradiated by light radiation during the transportation along a reaction line, whereby the quantity of light of a specified wavelength transmitted through the individual sample is measured by a spectrophotometer each cycle at different points in time, with increased processing speed, and with enhanced accuracy and precision.

Also in accordance with the present invention, the measurement by a spectrophotometer in a reaction channel is carried out independently from the washing and drying of the curvettes in a washing-drying channel, and both operations are conducted in parallel, whereby it is possible to take more time to wash and dry the cuvettes fully in order to prepare the cuvettes for the subsequent application.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
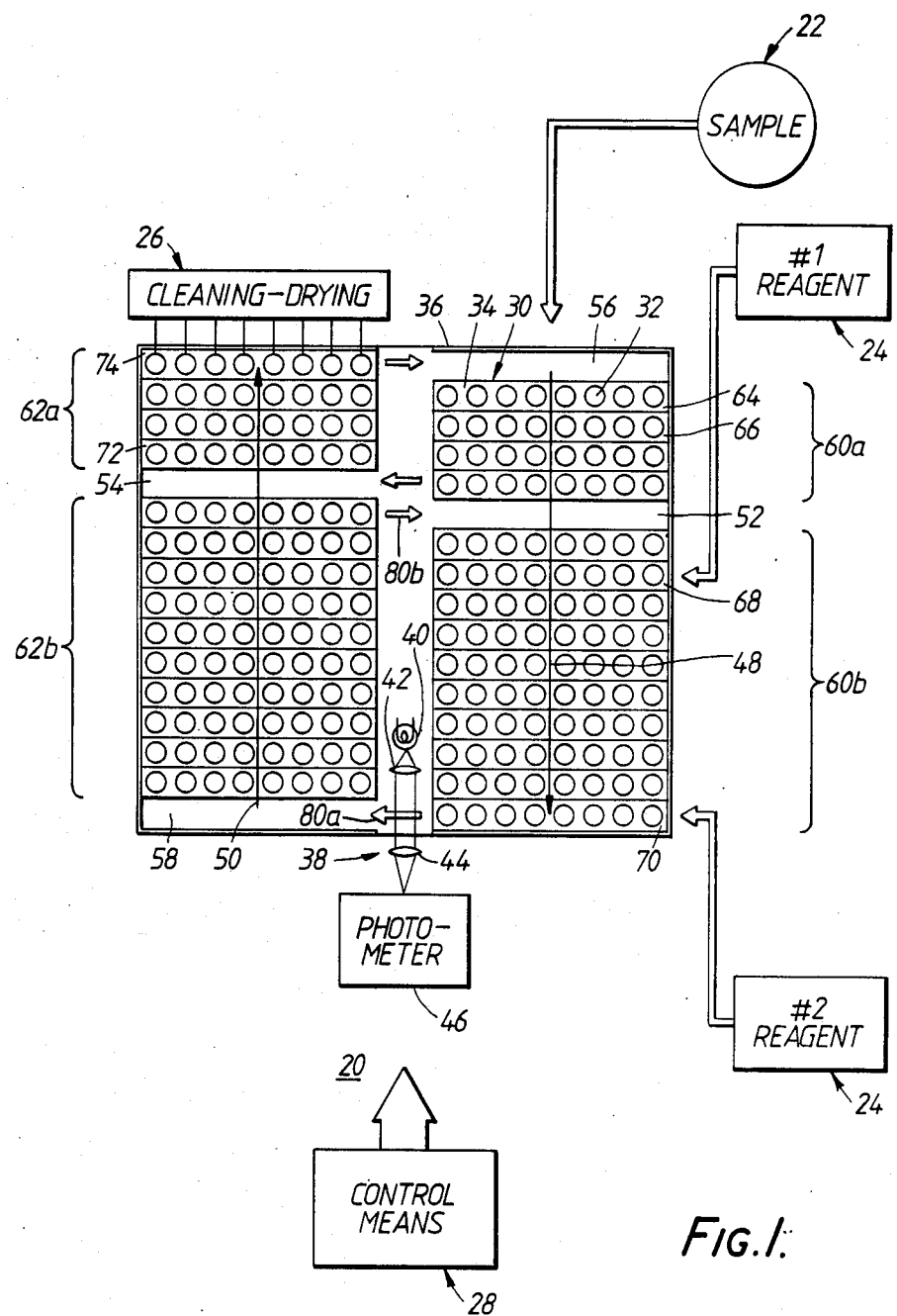
FIG. 1 is a diagram of an exemplary embodiment of an automatic chemical analyzing apparatus in accordance with the present invention.

Referring now to the drawings, wherein like reference numerals designate identical or corresponding parts in the several views, and referring particularly to FIG. 1, the automatic chemical analyzing apparatus of the present invention is indicated by the reference numeral 20 and generally includes (1) a cuvette assembly 30 which comprises a plurality of rows of open topped cuvettes or reaction tubes 32 arranged in sample magazines 34 of rectangular body shape, wherein the magazines 34 are made of metal such as aluminum blocks and are heated to a desired temperature, (2) a suitable heater 36 (typically an electric heater) which is positioned for heating the reaction tubes 32 through the magazine 34 to the desired temperature as required by the chemical tests being performed, (3) a readout or testing assembly 38 for analyzing the results of the chemical tests being performed, including a light source 40 having a filament that directs light throughout the visible and ultraviolet spectrum through a lens 42 through a window provided in the magazine 34 for each sample, through the sample in the reaction tubes 32, through a lens 44, and to a light measuring means such as photovoltaic cell 46, (4) a sampling dispensing assembly 22 for holding the sample to be tested and a pickup and dispensing apparatus for picking up the required amount of sample from the indexing table and dispensing each sample from the indexing table and dispensing each sample in a reaction tube 32 in the required amounts and for the tests programmed, (5) a reagent dispensing assembly 24 which may include a plurality of containers of reagents connected to metered dispensing units which in turn are connected to outlets positioned above the tubes 32 at the desired position or station on the reaction channel constructed by the cuvette assembly 30 for dispensing reagents in the proper sequence and at the proper station in the tests being performed, (6) tube drying and cleaning means 26 for drying the tubes 32 in preparation for reuse and recycling, and for cleaning the tubes 32 after the test has been concluded, and (7) suitable control means 28 for selectively controlling the sequential multiple analysis and synchronization of the above-mentioned components.

Referring again to FIG. 1, the construction of a preferred form of the reaction channel is best seen. The cuvette assembly 30 includes two rows 48, 50 of the sample magazines 34, each of which hold a transverse row of reaction tubes 32, the magazine 34 being periodically indexed a predetermined distance to move the tubes 32 from one position or station to the next so that the appropriate chemical steps may be performed upon the programmed samples at the proper station, time and sequence. The magazines 34 in each row 48, 50 are moved forward station to station in a direction perpendicular to the traverse row of reaction tubes 32, the direction of movement in each row being opposite to the other to construct a loop or circuit with these rows of the sample magazines 34.

Therefore, at the ends of the rows, the magazine 34 which reaches at that position is transferred to the other row by being pushed transversely by suitable means.

Further, a plurality of the sample magazines arranged one after the other in the rows 48, 50 are segmented by spaces 52, 54 equal to one sample magazine. Of course, the positions of these spaces 52, 54 against the heating means 36 are changable in accordance with the operation of the automatic chemical analyzing apparatus. Also, it is required to maintain a space between the end of each row 48 (50) and the heating means 36 of at least one sample magazine in order to transfer the single sample magazine 34 from one row to the other in accordance with the operation of the apparatus 20. Here, the space in the first row 48 is indicated by the reference numeral 56, the other in the second row 50 by the reference numeral 58. As will be understood from the foregoing description, these spaces are changed in position according to the movement of the loop in the apparatus 20.

When the tubes 32 are indexed to cleaning-drying segments 60a, 62a defining a preparation channel in both rows 48, 50, the tubes 32 are washed and cleaned. When the tubes 32 are indexed to reaction segments 60b, 62b defining a reaction channel in both rows 48, 50, the chemical reaction in the contents of the tubes 32 proceeds.

As shown in FIG. 1, the magazines 34 in the reaction segments 60b, 62b defining the reaction channel which continue to be forwarded in the circuit defined by the reaction channel are transferred at each end of the respective reaction row until the pretermined number of measurements for each magazine are concluded. Similar to movement in the reaction channel, the movement of the magazines 34 in the cleaning-drying channel 60a, 62a is carried out.

During movement of the cuvette assembly 30 in the direction indicated by the arrows 80a, 80b so as to be transferred from the first reaction segment 60b to the second reaction segment 62b at the ends, the samples contained in the reaction tubes 32 are successively projected by a light beam from the light source lamp 40 and the resulting transmissions through the tubes 32 are evaluated and recorded for analytical measurements using the photometer 46. The sampling dispensing assembly 22 dispenses a measured amount of sample into a reaction tube 32 at the proper positions or stations for performing the desired programmed tests, such as the position indicated by the reference numeral 66, and the various reagents required for the various chemical tests drawn from reagent containers (not shown) are dispensed into the reaction tubes 32 at the proper positions or stations and in the proper amounts. For example, the first reagent is dispensed into the reaction tubes which are indexed to a reagent station, such as the position indicated by the reference numeral 68, and the second reagent is added at the position indicated by the reference numeral 70.

After completion of chemical analysis, the magazines are transferred to the segment 62a in the preparation channel, by which the reaction tubes 32 in the magazine 34 are washed, and dried by suitable means 26 in preparation for rinse and recycling.

Operation of the System

Now referring to FIG. 2–8, the operation and movement of the automatic chemical analyzing apparatus according to the present invention will be described.

There is shown one embodiment of the cuvette assembly transporting operation which presents the cuvette assembly 30 to the proper position for sample dispensing, reagent dispensing, chemical analyzing, and for presentation to cleaning-drying stages of the tubes. In this embodiment, a number of cuvette magazines 34 are serially arranged in the first reaction row 48.

In this embodiment, the magazines 34 in the cuvette assembly 30 are moved a periodic distance after remaining in position for a set time interval by a transport means including sprockets and a continuous chain (not shown) arranged in an elongated circular pattern. The time required to move the magazine in the cuvette assembly 30 from one station to the next is referred to as the machine cycle time. It should be mentioned that, in the discrete type automatic analyzing apparatus like the present invention, the chemical controls or manipulations such as photometry, sampling dispensing, reagent dispensing, washing or the like can be carried out within the above machine cycle time for a sample. One cycle is to be completed within the predetermined time duration, such as 10 seconds.

Figure 2:
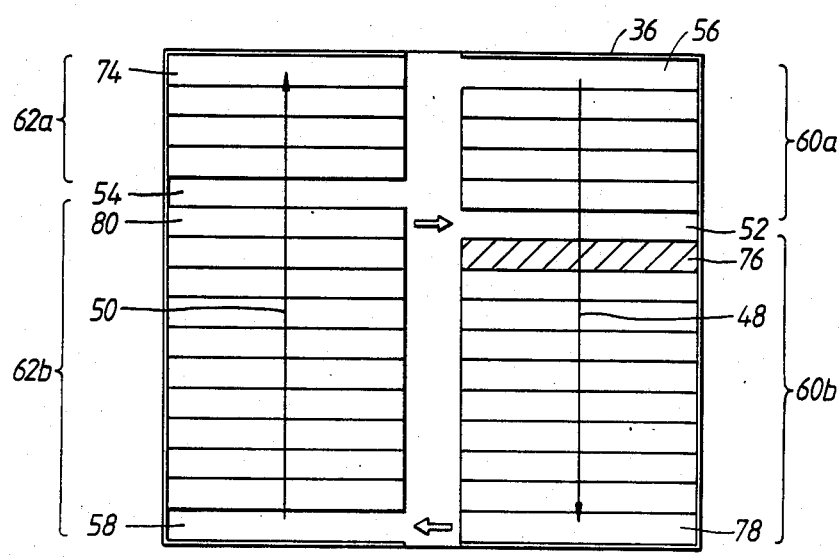
FIG. 2 is schematic diagram illustrating operation of the automatic chemical analyzing apparatus of the invention in the performance of photometry for the samples in the cuvette assembly.

In FIG. 2, after the magazine receiving new samples added with the preselected first reagent in the reaction tubes is moved to the position 76 in the first reaction segment 60b, the magazine 34 in the end position 78 of the first reaction segment 60b is moved toward the end position 58 of the second reaction segment 62b. Simultaneously the magazine 34 in the other end position 80 of the reaction segment 62b is moved back to the position 52 in the reaction segment 60b. The foregoing cycle of operation continues until each of the samples has been analyzed during the preselected time interval, for example 5 minutes. On this cycle, the samples contained into the reaction tubes 32 of the magazine 34 in the position 78 are measured by the photometer 38 by impingment with the light beam during movement to the position 58.

Figure 3:
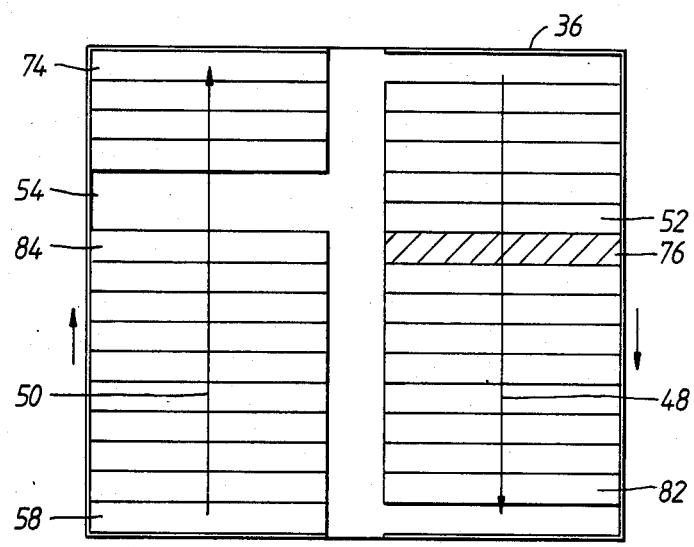
FIG. 3 is a schematic diagram illustrating operation of the automatic chemical analyzing apparatus of the invention is the forwarding of the cuvette assembly after the photometry.

In FIG. 3, on the cycle sequential to the foregoing cycle, all the magazines 34 in the positions 52–82 are forwarded by a step and simultaneously the magazines 34 in the positions 58–84 are forwarded by a step.

These two operations are continuously repeated until the photometry for certain samples contained in a single magazine has been concluded by times corresponding to the number of the magazines positioned in the reaction segments 60b, 62b as previously described. Thus, the arrangement of the cuvette assembly 30 returns to the condition shown in FIG. 1.

The predetermined measurement being finished for the samples in a certain magazine 34 as understood from the foregoing description, the magazine containing a samples analyzed and a magazine 34 prepared for chemical analysis of other samples are exchanged between the preparation channel 60a, 62a and the reaction channel 60b, 62b.

Figure 4:
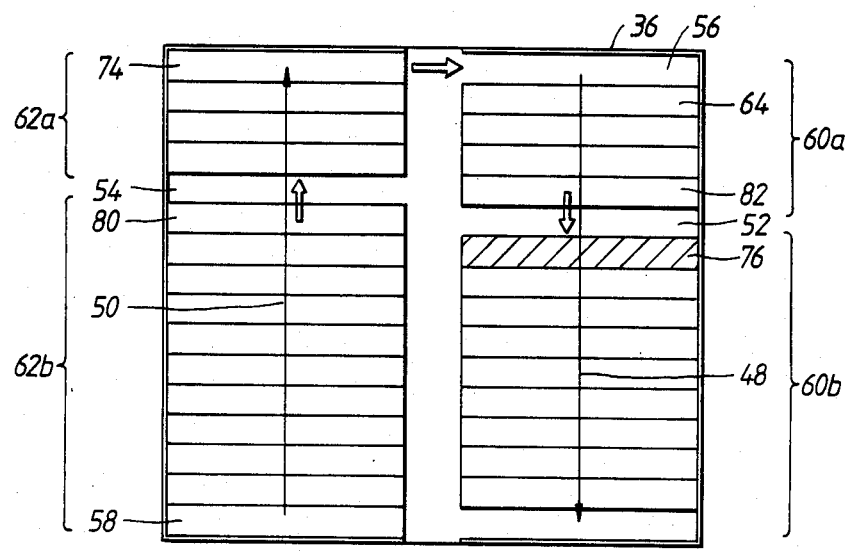
FIG. 4 is a schematic diagram illustrating an operation of the automatic chemical analyzing apparatus of the invention in the transfer of the cuvette assembly between the cleaning-drying and reaction channels.

Referring to FIG. 4, first, the magazine 34 in the position 80, the analysis of which has been completed, can be routed from to the segment 62b of the reaction channel to the segment 62a of the preparation channel. At the same time, the magazine 34 in the position 74 of the preparation channel segment 62b is transferred to the position 56 of the first preparation channel segment 60a. Then, the cuvette assembly 30 in the position 82 of the first cleaning-drying channel 60a, which has samples and reagents mixed to be analyzed, can be transferred from the cleaning-drying channel segment 60a to the reaction channel segment 60b. Thereby, the magazine 34 in the position 82 is moved to the position 52 of the reaction channel segment 60b.

Figure 5:
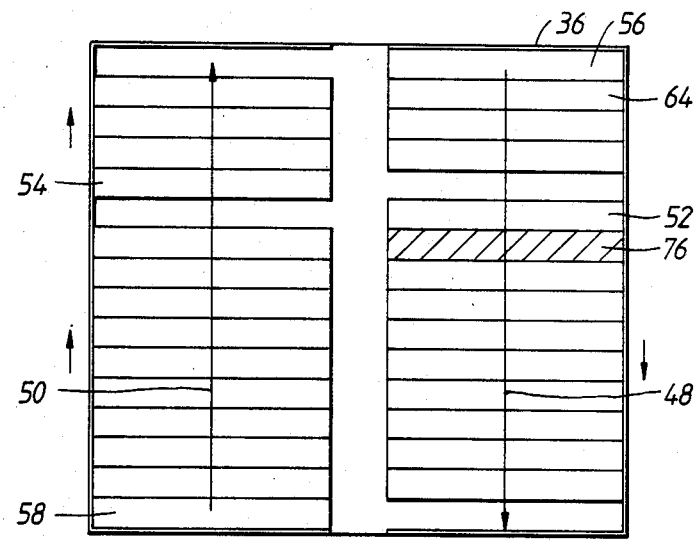
FIG. 5 is a schematic diagram illustrating an operation of the automatic chemical analyzing apparatus of the invention in returning the arrangement of the cuvette assembly to the beginning condition of a measuring cycle.
Figure 6:
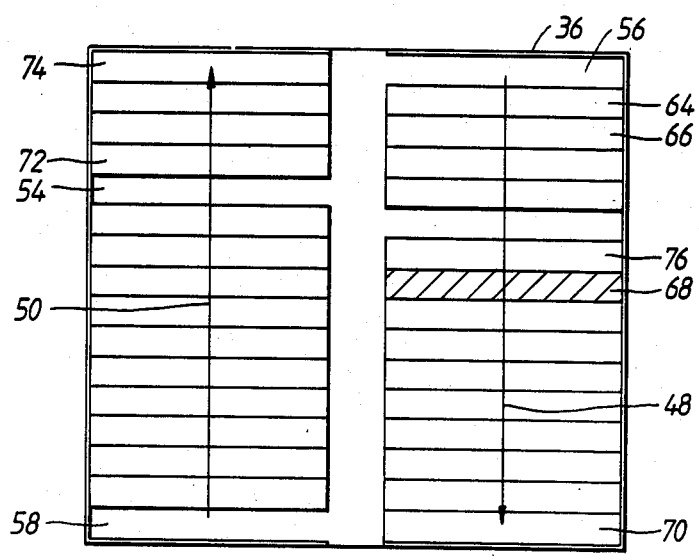
FIG. 6 is a schematic diagram illustrating operation of the automatic chemical analyzing apparatus of the invention in completing one measuring cycle for a certain number of samples.

The arrangement of the cuvette assembly 30 in this apparatus after the above operation is done is seen in FIG. 5. All the cuvettes arranged in the heating means 36 as shown in FIG. 5 are moved clockwise by a step. Finally, the magazine 34 which was in the position 76 of the first reaction channel segment 60b at the beginning of the first reaction cycle shown in FIG. 2., is moved to the successive position 68 as shown in FIG. 6. In accordance with the operations as above described, one cycle needed to analyze the chemical reactions over the required period to achieve an accurate measurement of the samples is completed. While the magazine 34 is in the position 68 of the reaction channel segment 60b (the second reagent adding station), the second reagent is added into the reaction tubes 32 thereof by suitable reagent dispensing means.

As understood from the above mentioned operations, the counterclockwise movement of the cuvette assembly 30 in the cleaning-drying channel 60a, 62a can proceed slowly or, on the contrary, the movement of the cuvette assembly 30 in the reaction channel 60b, 62b can be fast to improve significantly sample processing capability. Therefore, more time can be spent to prepare for the selected chemical analysis, such as cleaning, drying of the reaction tubes, sampling dispensing, reagent dispensing, etc., during the time that measurement for other samples is carried out in the reaction channels 60b, 62b. It is very important to eliminate the contamination between the different samples, or reagents by completing the cleaning-drying of the tubes 32.

Figure 7:
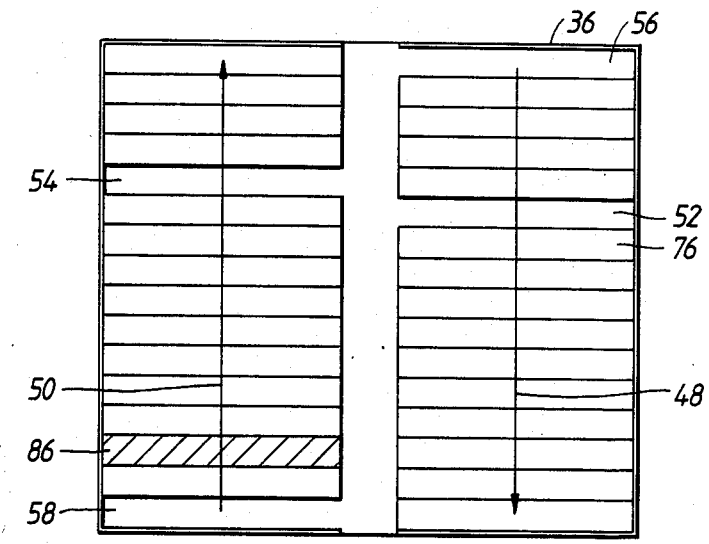
FIG. 7 is a schematic diagram illustrating an alternative embodiment of the present invention, and shows the position of the subject cuvette assembly at the end of a measuring cycle.
Figure 8:
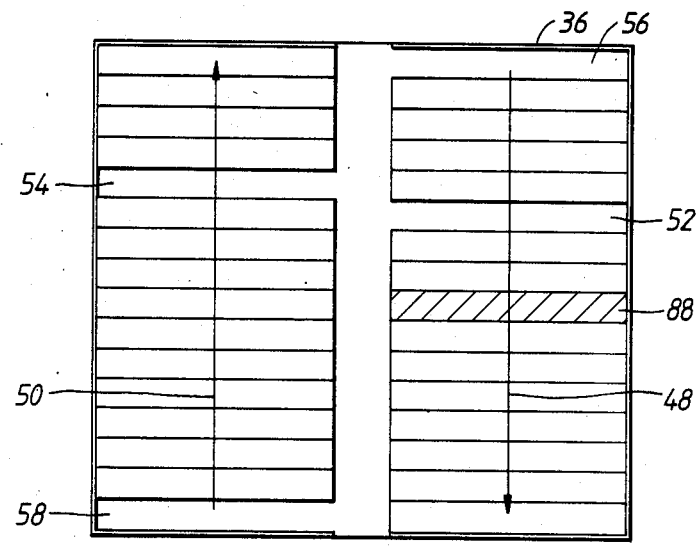
FIG. 8 is a schematic diagram illustrating the alternative embodiment of the present invention, and shows the arrangement of the subject cuvette assembly at the beginning of the following measuring cycle to the cycle shown in FIG. 7.

Referring to FIGS. 7–8, there is seen on alternate embodiment of the present invention wherein the processing capability is increased by sacrificing the measurement times by the photometer 38. In the first embodiment, one measuring cycle includes the operations described before until the time that the cuvette assembly 30 is clockwise revolved in the reaction channel segments 60b, 62b by one revolution and further forwarded by one step. In the alternative embodiment, one measuring cycle is completed without one revolution of the cuvette assembly in the reaction channels 60b, 62b.

During the time that the cuvette assembly 30 is moved from the position 76 of the first reaction channel segment 60b at the beginning of the measuring cycle to the position 86 in the second reaction channel segment 62b (shown in FIG. 7) in accordance with the operations as described previously, the magazine with cuvettes to be analyzed passes through detection station (photometer 38). Then the photometry for the samples contained in the cuvette assembly 30 is carried out during the times corresponding to the number of the cuvettes included in the magazines arranged between the positions 76–86.

After the analyses for given samples have been concluded in the detection station, a new magazine 34 containing other samples added with reagent will be immediately transferred to the reaction channel segment 60b from the preparation channel segment 60a. Simultaneously, the magazine 34 for which the measurement has been completed will be routed from the reaction segment channel 62b to the preparation channel segment 62a. It should be appreciated that there will simultaneously be many magazines at various stations within the apparatus. By simultaneously, it is not meant that the beginning and end of each operation coincides with the beginning and end of other operations, but rather that there is a substantial overlapping of the operational steps involved. Thus, one magazine 34 will be in the sample dispensing station while another will be in the detection station.

At a subsequent cycle, the magazine 34 moved toward to the position 68 (shown in FIG. 6) during the previous cycle will be in the position 88 shown in FIG. 8 by being revolved clockwise by the predetermined steps. During the cycle the magazines 34 will be exchanged between the reaction channel 60b, 62b and the preparation channel 60a, 62a.

While the invention has been described with reference to preferred embodiments thereof, it will be understood by those skilled in the art that various changes in form and details may be made without departing from the true spirit and scope of the invention. Many alternate embodiments can be conceived which will achieve the advantageous results herein disclosed. For example, the reaction mixture contained in the magazine 24 can be analyzed by passing once through the photometer 38 prior to entering the preparation channel or it can be designed that the magazine 24 containing samples to be analyzed passes the detection station several times before entering the preparation channel.

However, there is a restriction in selecting the number n of magazines in each reaction channel segment arising from the relationship with the stepping of the cuvette assembly 30. The meaning of step used in this application is the movement of the cuvette assembly 30 in sequence for each operation.

Now, supposing the number of magazine arranged in the reaction channel 60b, 62b is 2n; the number of steps to complete one cycle for a given measurement of sample is p, i.e., p equals the number of stations a magazine advances in the reaction channel between an exchange of magazines between the reaction and preparation channel, the magazine after completing the measurement should be routed from the reaction channel segment 62b to the preparation channel segment 62a at the 2nth cycle, neither prior, nor after that. Therefore, p may not be either an even number or a whole number odd divider of the total number N (N=2n) of magazines in the reaction channel. For example, if n=6, 2n=N=12, then p may not equal even numbers 2,4,6,8,10 or 12 or whole number odd divider 3. Similarly if n=15, N=2n=30, then p may not equal even numbers or 3,5 or 15.

Further, in case of p>2n, p minus a multiplicative number of 2n can be satisfied with the above condition by selecting the appropriate number for p.

It is contemplated that any analytical procedure can be adapted to the invention herein disclosed. While the apparatus and system herein disclosed is particularly suitable for routine and stat blood chemistry, such as glucose etc., numerous other analytical tests which are run periodically in any chemical environment can be automatically performed in accordance with the aforesaid disclosure.

Accordingly, all substitutions, additions, and modifications to which the present invention is readily susceptible, without departing from the spirit and scope of this disclosure, are considered part of the present invention.

What is claimed as new and desired to be secured by Letters Patent of the United State is:

1. An automatic chemical analyzing apparatus comprising:

a cuvette assembly comprising a preparation channel and a reaction channel including first and second segments, and third and fourth segments, respectively, of sample magazines, each of said segments being parallel to one another and including a transfer station, each of said segments containing a plurality of magazines, each magazine including a plurality of reaction tubes arranged in a direction transverse to a line along which the segments of the preparation and reaction channels are arranged, wherein the magazines of said preparation channel are capable of being moved in and between said first and second segments by being moved sequentially from one station to a next station and from said first segment to said second segment and vice versa around a preparation circuit including said first and second segments, and the magazines of said reation channel are capable of being advanced in and between said third and fourth segments of being moved sequentially from one station to a next station and from said third segments to said fourth segment around a reaction circuit including said third and fourth segments;

conveying means for independently advancing the magazines of the preparation channel around said preparation circuit and for independently advancing the magazines of the reaction channel around the reaction circuit;

means for transferring magazines in said preparation channel to said reaction channel and for transferring magazines in said reaction channel to said preparation channel;

said preparation channel comprising:

means for cleaning and drying the tubes of each magazine transferred to said preparation channel upon transfer of each magazine from the reaction channel to said preparation channel for reuse and recycling of the cleaned and dried tube, sample dispensing means located along said preparation circuit after said cleaning and drying means for dispensing a sample to be analyzed to the cleaned and dried tubes, and heating means located adjacent to said sample dispensing means in said preparation circuit for heating said samples;

wherein sadi trnasferring measn transfers magazines having heated samples to said reaction channel;

said reaction channel comprising, reagent dispensing means located at a predetermined station of said reaction channel for adding at least one reagent to selected tubes transferred to said reaction channel from said preparation channel, and a testing assembly located at a predetermined position along said reaction channel for analyzing the contents of said tubes as said tubes advance in said reaction channel; and control means for controlling the movement of said magazines in said preparation channel independently of the movement of said magazines in said reaction channel, said control means including means for determining which stations of said first through fourth segments are transfer stations between which magazines are exchanged segment-to-segment in dependence on the number of magazines in said reaction channel, and means for controlling said transferring means to transfer a particular magazine from said reaction channel to a determined transfer station of said preparation channel upon completion of analyzing by said analyzing means of the samples contained in said particular magazine;

wherein said first and third segments are arranged along a first common line and said second and fourth segments are arranged along a secodn common line, and said transferring means transfers magazines from said second segment to said fourth segment and from said third segment to said first segment upon transferring magazines between said preparation and reaction channels, and transfers magazines between said first and second segments and between said third and fourth segments for intrachannel transfer of magazines.

2. The automatic chemical analyzing apparatus of claim 1, comprising:

control means for controlling the speed of movement in said channels such that when in said preparation channel, the magazines are advanced at one speed, and when in said reaction channel, the magazines are advanced at a speed faster than said one speed.

3. The automatic chemical analyzing apparatus of claim 1, wherein said tesing assembly is positioned between said third and fourth segments of sample magazines to analyze said samples during a time when the magazine is transferred from one of said third and fourth segments to the other of said third and fourth segments.

4. The automatic chemical analyzing apparatus of claim 3, wherein said transferring means comprises:

control means for transferring a magazine from said reaction channel to said preparation channel after the magazine has passed through said testing assembly a predetermined number of times.

5. The automatic chemical analyzing apparatus of claim 4, wherein said reagent dispensing means comprises:

a reagent addition station for adding at least one reagent to the samples in a magazine in said preparation channel.

6. The automatic chemical analyzing apparatus of claim 5, wherein said speed controlling means advances said magazine containing samples to be analyzed in said reaction circuit to monitor the results of the chemical tests for a period of time sufficient to analyze each sample.

7. An analyzing apparatus according to claim 1, wherein said control means comprises:

means for synchronizing operation of said transferring means and said conveying means such that just prior to transferring magazines between said preparation and reaction channels, said first segment has an empty transfer station at the end thereof adjacent said third segment and said fourth segment has an empty transfer station at one end thereof adjacent said second segment, said transferring means then transferring under the control of said control means a magazine from said third segment to said empty transfer station of said first segment and a magazine from said first segment to said empty transfer station of said second segment, said conveying means under control of said control means advancing each magazine in said preparation and reaction channels upon transfer of magazines between said channels such that after said transfer of magazines, an empty transfer station exists at the end of said second segment opposite the end thereof adjacent said foruth segment and an empty transfer station exists at the end of said third segment opposite the end of said third segment adjacent said first segment.

8. The uatomatic chemical analysis apparatus according to claim 7, wherein said reaction channel comprises $2n$ magazines, where $n$ equals the number of magazines in each segment of the reaction channel, and wherein said control means comprises:

means for controlling said conveying means and said transferring means such that the magazines in said reaction channel are advanced from station to station a total of $p$ stations before magazines are transferred between the reaction channel and preparation channel, wherein $p$ is limited only to odd numbers, exclusive of odd whole number dividers of $2n$.

* * * * *